United States Patent [19]
McCroskey et al.

[11] Patent Number: 5,751,000
[45] Date of Patent: May 12, 1998

[54] PREFILTER COLLIMATOR FOR PET GAMMA CAMERA

[75] Inventors: William K. McCroskey, Solon; David S. Vickers, Independence, both of Ohio

[73] Assignee: SMV America, Inc., Twinsburg, Ohio

[21] Appl. No.: 780,642

[22] Filed: Jan. 8, 1997

[51] Int. Cl.⁶ .......................... G01T 1/161; G01T 1/164
[52] U.S. Cl. ........................ 250/363.03; 250/363.02
[58] Field of Search ..................... 250/363.03, 363.04, 250/369, 363.02; 378/147, 149

[56] References Cited

U.S. PATENT DOCUMENTS

| | | |
|---|---|---|
| 4,323,779 | 4/1982 | Albert . |
| 4,528,453 | 7/1985 | Heller . |
| 5,239,568 | 8/1993 | Grenier . |
| 5,381,012 | 1/1995 | Kutolowski . |
| 5,512,754 | 4/1996 | Enos . |
| 5,585,637 | 12/1996 | Bertelsen et al. .................. 250/363.03 |
| 5,608,221 | 3/1997 | Bertelsen et al. .................. 250/363.03 |

*Primary Examiner*—Michael J. Tokar
*Assistant Examiner*—Richard Hanig
*Attorney, Agent, or Firm*—Frank J. Nawalanic

[57] ABSTRACT

A gamma camera is equipped with a graded filter plate in lieu of a collimator so that the gamma camera can perform PET studies. The filter plate prevents detection of Compton scattered, positron annihilation photons produced in the patient while permitting detection of photons which have experienced Compton scattering within the camera's scintillation crystal to significantly increase the camera's usable count rate. Additionally, the filter is fitted with a protruding baffle shielding the camera from stray 511 Kev radiation.

14 Claims, 7 Drawing Sheets

PREFILTER COLLIMATOR FOR PET GAMMA CAMERA

This invention relates generally to gamma cameras conventionally used to perform SPECT studies and more particularly to such a camera used to conduct PET studies.

The invention is particularly applicable to and will be described with specific reference to a gamma camera which is capable of conducting both PET and SPECT studies. However, those skilled in the art will appreciate that the invention has broader application and may be applied to conventional PET scanners to improve the imaging time, the resolution and efficiencies of such scanners.

INCORPORATION BY REFERENCE

Our application filed as of this date entitled Gamma Camera for PET and SPECT Studies and assigned to the present assignee, SMV, is incorporated herein. The invention disclosed and claimed herein is believed separate and distinct from that disclosed and claimed in our application filed concurrently herewith.

In addition, the following documents are incorporated by reference herein (as well as documents incorporated or referred in such documents) so that the Detailed Explanation of this invention need not state in detail that which is known to those skilled in the art. The additional documents incorporated by reference herein do not form part of the present invention.

U.S. Pat. No. 5,512,754 to Gary W. Enos, (assigned to SMV, the assignee of this invention) issued Apr. 30, 1996 entitled "Filtered Collimator for Dual Isotope Medical Imaging";

U.S. Pat. No. 5,381,012 to Paul C. Kutolowski, (assigned to SMV the assignee of this invention) issued Jan. 10, 1995 entitled "Collimator Transfer System for a Nuclear Camera";

U.S. Pat. No. 5,239,568 to Raymond P. Grenier, issued Aug. 24, 1993 entitled "Radiation Collimator System";

U.S. Pat. No. 4,528,453 to Sherman L. Heller, issued Jul. 9, 1985 entitled "Dual Collimator" and U.S. Pat. No. 4,323,779 to Richard D. Albert, issued Apr. 6, 1982 entitled "Scanning Radiographic Method".

BACKGROUND OF THE INVENTION

Nuclear or scintillation or gamma cameras originally developed by Anger are conventionally used to perform Single Photon Emission Computed Tomography ("SPECT") studies. A patient ingests a radiopharmaceutical, such as Thallium or Technetium, which emits gamma radiation from a body organ which is the subject of a medical study. The gamma camera detects the radiation and generates data indicative of the position and energy of the radiation which is then mathematically corrected, refined and processed through a procedure known as reconstruction tomography (performed by a computer) to produce pictures of scintigrams (two or three dimensional) of the body organ which is the subject of the study.

Different radiopharmaceuticals produce gamma rays having different energies typically expressed as a photopeak energy in electron volts corresponding to the output pulse generated by a photomultiplier ("PMT") in response to a scintillation produced by the crystal when struck by a gamma ray. Gamma cameras are fitted with removable lead collimators having varying thicknesses for collimating gamma rays of various energies. Collimators in gamma cameras, however, do not straighten the gamma rays. They simply absorb angular rays in the septa so that only parallel rays pass through and strike the crystal. For higher energy gamma rays, the thickness or depth of the passages or channels in the collimator have to increase to absorb the cross channel and slightly angular rays which would otherwise pass through the collimator. Gamma cameras are thus typically supplied with thin, medium and thick removable collimators sized to cover the energy spectrum of the gamma radiation used in SPECT studies.

A typical gamma camera is fitted with two detector heads, each of which is fitted with a collimator and each head extends in a two dimensional plane, referred to herein as the x,y plane. Each head contains an array of photomultipliers which are arranged behind a scintillation crystal which is almost always, a sodium iodide crystal doped with Thallium. The PMT's generate analog pulse signal in response to the scintillations produced by the crystal when struck with gamma rays passing through the collimator which indicate the energy of the gamma ray, i.e., the photopeak signal. The pulse signals are grouped, digitized, corrected and processed as data indicative of position, x,y and energy, z. This data correlates to a pixel of a 2-d picture spanning or encompassing the area of the detector head. A two head gamma camera will simultaneously generate two such pictures or scintigrams (a 3 head camera will generate 3 pictures, etc), each of which may be viewed as being similar to an x-ray. The heads will then typically rotate about the body and generate additional pictures which are then assembled together to make a 3-d view of the object precisely pinpointing the shape of any abnormality emitting gamma radiation within the organ.

A PET study is fundamentally different. In a PET study, radionuclides, typically fluorine-18, carbon-11, nitrogen-13 or oxygen-15 are incorporated into substances such as glucose or carbon dioxide to produce radiopharmaceuticals such as FDG (Fluorine-Deoxy-Glucose) which are ingested by, or injected into, the patient. As the radionuclides decay, positrons are emitted and they collide, in a very short distance, with an electron and become annihilated and converted into two photons, or gamma rays, traveling linearly in opposite directions to one another with each ray having a photopeak energy of about 511 Kev. By detecting the exact position where each coincident pair photon struck, at about the same time, opposing scintillation crystal, a line of response ("LOR") can be generated through the two points. By accumulating a number of LORs, an image can be constructed.

Relatively expensive (when compared to the cost of a gamma camera) imaging apparatus, known as a Pet scanners, have been developed solely to perform PET studies. PET scanners typically comprise, laterally spaced rings, each of which encircles the patient. Detectors, typically PMTs, continuously extend about each ring and a scintillation crystal, typically BgO, is placed in front of the detectors. The detectors thus form a single line or a one dimensional array extending about the patient and collimators are not needed nor are they typically employed in PET scanners. That is, because the one dimensional array completely encircles the patient, the solid or included angle of the arrangement is 360° and all positron annihilations occurring in that one dimensional plane are captured. Thus the PET scanner typically captures all LORs occurring within a slice of the object and the slices of the objects are stacked (as the rings shift and take different slices) in the tomography reconstruction process to assemble a 3-d image.

While the literature will sometimes mention that gamma cameras can perform PET studies, the basic 2-d geometry of the detector head generates a small solid angle which has been found, in practice, totally inadequate with collimators to accumulate a sufficient number of positron annihilation events or counts to construct an image within a reasonable time. With the collimators removed a significant amount of Compton scattered events overwhelm the detector's electronics making it difficult to discern true coincident events. This failure to obtain a sufficient number of coincident counts within a reasonable time which is inherent in the basic geometry of the gamma camera is believed to be the primary reason why, until this invention, gamma cameras have not been utilized to perform PET studies. Otherwise, on the basis of cost considerations alone, the industry would have long adopted the gamma camera in lieu of PET scanners.

It is well known that the photons resulting from a positron annihilation will experience attenuation within the organ attributed to Compton scattering. It is also known that the gamma ray photons will also experience attenuation attributed to Compton scattering within the scintillation crystal. Because of the high angular deflections attributed to Compton scattered rays originating outside the crystal, it is not possible to accurately match Compton scattered rays with 511 Kev photopeak energy waves to determine a coincident event. Thus, many conventional PET scanners discard the Compton scattered events and match only photons having photopeak energies of about 511 Kev in their coincidence detecting circuits. Again, PET ring scanners, because of their solid angle, acquire a sufficient number of 511 Kev counts for adequate image resolution.

Conventional camera and scanner detection techniques use any number of mathematical techniques and formula (pulse shape discrimination, i.e., PSD) to differentiate pulses produced by different types of particles. However, the photopeak energy of a Compton scattered ray occurring within the patient is, for all intents and purposes, the same photopeak energy as that occurring within the crystal. PSDs thus cannot reliably discriminate scintillations resulting from particles which have experienced attenuation attributed to Compton scattering occurring outside the crystal from those which occurred within the crystal. PSDs can, however, effectively remove Compton scattered rays from the coincidence window.

Hardware approaches have been developed to eliminate Compton scattered radiation from the determination of a pair production event. One approach described in the literature utilizes a Compton-suppression spectrometer which uses two detectors operated in anticoincidence to eliminate, like the PSDs, scintillations attributed to Compton effect particles. One specific arrangement uses a larger NaI(TI) scintillator which surrounds a s Ge(Li) detector. When the two detectors are operated in anticoincidence, the center Ge(Li) detector will consist of pulses that result from total energy absorption in that detector. (Measurement and Detection of Radiation, Nicholas Tsoulfanidids, published by Hemisphere Publishing Corporation, 1983, pages 357–360).

In general, it has long been known in radiology to use filters to "harden" the radiation beam so that the X-ray beam contains a higher percentage of higher energy, more penetrating photons. It has also been known with monoenergetic radiation, such as cobalt 60 gamma rays, that filters can be used as beam-flattening devices. Various compound filters such as the Thoreaus filter are used to increase the radiation exposure rate (The Fundamentals of X-Ray and Radium Physics, 7th Edition, Joseph Selman, published by Charles C. Thomas, 1985, pages 207–209). Filters have been placed in the path of the radiation beam to attenuate the beam.

Additionally, it is known in the gamma camera art to simultaneously acquire data from two or more isotopes ingested by the patient and SMV's U.S. Pat. No. 5,512,754 used a filter arrangement within a collimator to permit simultaneous imaging of two spectrally close isotopes, Thallium and Technetium, so that the heart's response to stress and the heart's recovery from stress could be measured in one study.

SUMMARY OF THE INVENTION

Accordingly, it is a principal object of the invention to provide a prefiltering collimator for use with a gamma camera to significantly increase the ability of the gamma camera to detect positron annihilation events.

This object along with other features of the invention is achieved in a gamma camera capable of performing PET studies having at least first and second detector heads with each detector head having a scintillation crystal and a plurality of photomultipliers adjacent one another on one side of the crystal producing pulse signals indicative of the intensity of scintillations produced by the crystal when struck by photons resulting from positron annihilation events. The camera includes a somewhat conventional signal triggering mechanism for determining when the pulse signal of any given photomultiplier becomes a triggering signal having at least a set photopeak energy and a somewhat conventional coincidence detecting arrangement for determining when any given triggering signal from one detector head occurs within a preset time of any given triggering signal from the other detector head to establish a matched pair of triggering signals indicative of a positron annihilation event which are then refined and corrected so that tomographic PET images can be produced. Importantly, each crystal has on its side facing the patient, a filter extending over the area of the crystal. The filter has an atomic number Z and thickness sufficient to absorb photons resulting from positron annihilations which have experienced attenuation attributed to Compton scattering outside the crystal to a value not detected by the signal triggering means whereby photons having photopeak energies of about 511 Kev which experience filter attenuation and which also experience further attenuation attributed to the Compton effect within the crystal will nevertheless actuate the signal triggering mechanism to significantly increase the count of the positron annihilation events recorded by the camera.

In accordance with another important feature of the invention each detector head includes a body housing containing its crystal and photomultipliers and a frame removably secured to the body housing. The frame contains the filter and has a continuous, shielding baffle circumscribing the filter adjacent the peripheral edge of the filter and protruding away from the body housing whereby the baffle is adapted to be positioned in close proximity to the imaged patient's body organ for shielding the detector head from stray radiation, specifically stray radiation having photopeak spectral energies of about 511 Kev.

In accordance with another specific but important feature of the invention, the filter reduces the scattered counts thereby increasing the ratio of true coincident events to total events.

It is a principal object of the invention to significantly increase the usable count rate detected by a gamma camera when performing PET studies.

It is another object of the invention to provide a gamma camera capable of performing PET studies which has a modified detector head preventing stray radiation from impacting the scintillation crystal to adversely effect the detection of valid positron annihilation events by the camera.

It is yet another object of the invention to provide in a gamma camera a filter plate in lieu of a conventional lead collimator.

Still another object of the invention is to provide a gamma camera with a filter in a removable frame whereby the gamma camera fitted with the filter can perform PET studies and with the filter removed and replaced with a conventional collimator perform a normal SPECT study.

It is still another object of the invention to use a filter plate in front of the scintillation crystal in a gamma camera which is to perform a PET study so that the same thallium doped sodium iodide scintillation crystal can be used in the gamma camera during both SPECT and PET studies.

A general but important object of the invention directly attributed to the use of a filter plate is that a low cost gamma camera can now replace expensive conventional PET scanners otherwise required to perform PET studies.

Still yet another object of the invention is to provide a filter plate in a transfer frame which can be easily applied to the gamma camera in lieu of the lead collimator and which thus permits existing gamma cameras to be retrofitted with PET imaging capabilities.

These and other objects, features and advantages of the invention will become apparent from the following Detailed Description of the invention taken together with the accompanying drawings.

BRIEF DESCRIPTION OF THE DRAWINGS

The invention may take form in certain parts and arrangement of parts, a preferred embodiment of which will be described in detail herein and illustrated in the accompanying drawings which form a part hereof and wherein.

DETAILED DESCRIPTION OF THE INVENTION

Figure 1:
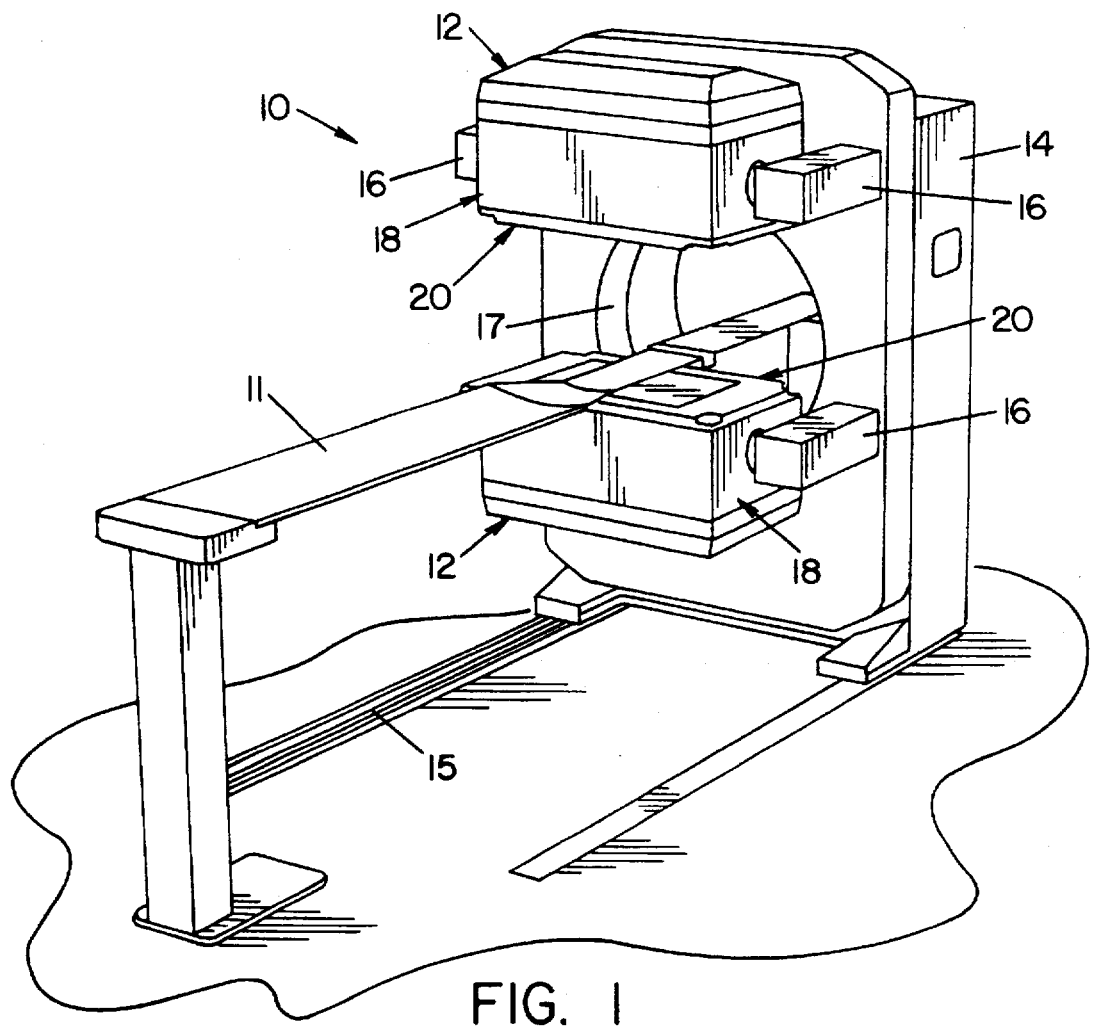
FIG. 1 is a perspective of a gamma camera.

Referring now to the drawings wherein the showings are for the purpose of illustrating a preferred embodiment of the invention only and not for the purpose of limiting same, there is shown in FIG. 1 a gamma camera 10 which includes a table 11 on which a patient lies so as to position a body organ between two detector heads 12. In the preferred embodiment two detector heads are utilized. However, gamma cameras can be fitted with three or four detector heads and, in theory, the invention will work with multiple detector heads. In practice, only two detector heads are used.

Detector heads 12 are mounted to a gantry 14 movable on tracks 15 to position detector heads 12 along the length of the patient. In addition, detector heads 12 are carried by arms 16 which are movable towards and away from one another and the patient for camera focusing (and establishing line of response distances through a conventional encoder mechanism not shown). Arms 16 are carried by a rotatable frame 17 within gantry 14 which permit detector heads 12 to rotate about the patient for image acquisition purposes.

Figure 2:
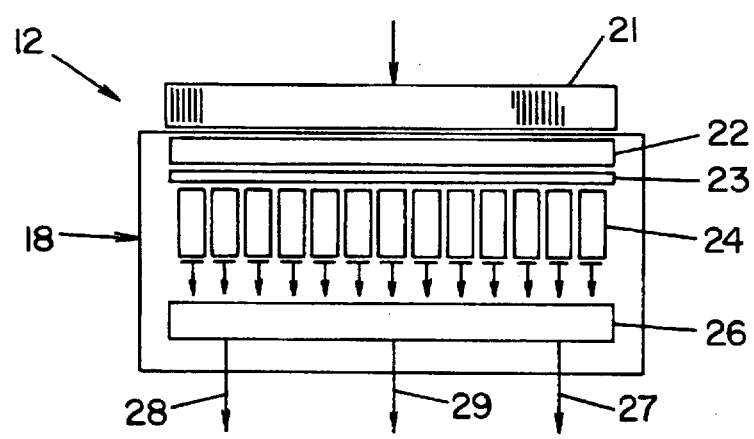
FIG. 2 is a schematic view of the detector head of a gamma camera.

Referring now to FIG. 2, each detector head 12 includes a detector housing 18 onto which a removable collimator frame 20 which, in turn, typically contains a lead collimator 21. Fixed within detector housing 18 a scintillation crystal 22 which abuts collimator 21. On the opposite side of scintillation crystal 22 is positioned a light pipe 23 which, in turn, is incident upon the face plates of a plurality of photomultiplier tubes (PMTs) 24. In the preferred embodiment, 58 PMTs 24 are mounted within detector housing 18 tightly adjacent one another. Typically, face plates of PMTs 24 are hexagonal so that the bundle of 58 PMTs 24 can present a continuous surface behind scintillation crystal 22 to receive all scintillations produced by scintillation crystal 22. PMTs 24, in turn, generate electrical pulse signals and reference can be had to assignee's (SMV's) U.S. Pat. No. 5,512,755 for a description of how each PMT 24 develops its pulse signal. Signal processors 26 conventionally detect valid pulse signals indicated generally by reference numeral 27 and each valid pulse signal 27 is assigned a two-dimensional position, i.e., x,y, indicated generally by reference numeral 28. For each valid pulse signal 27 signal processors also determine an energy or z value correlated to the intensity of the detected scintillation, indicated generally by reference numeral 29. Those basic signals 27–29 are then corrected and refined to produce data which is subsequently used to generate tomographic images.

Figure 3A:
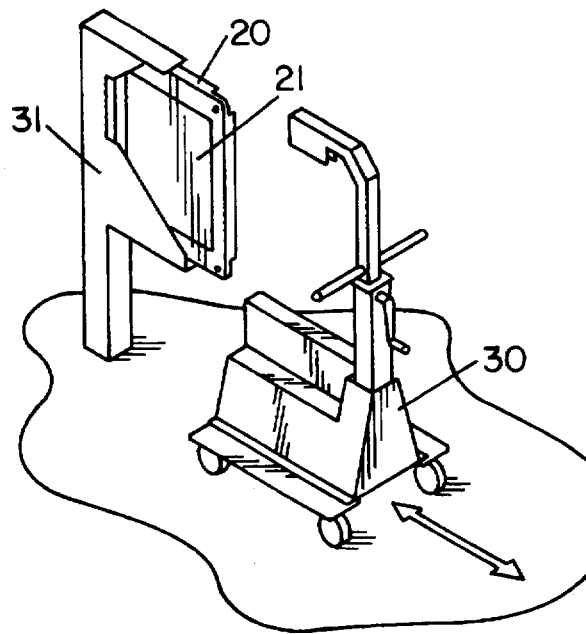
FIG. 3A is a perspective view of a transfer cart and a collimator used with the gamma camera.
Figure 3B:
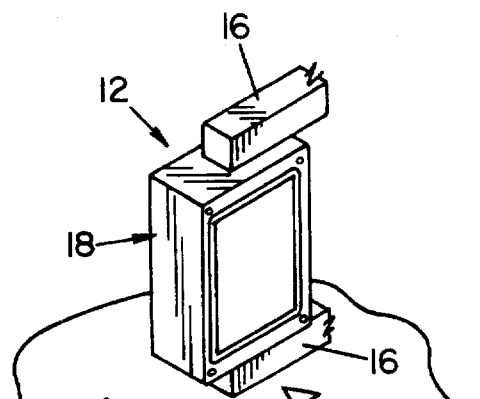
FIG. 3B is a perspective view similar to FIG. 3A showing the cart with collimator moving to the gamma camera's detector head.
Figure 3C:
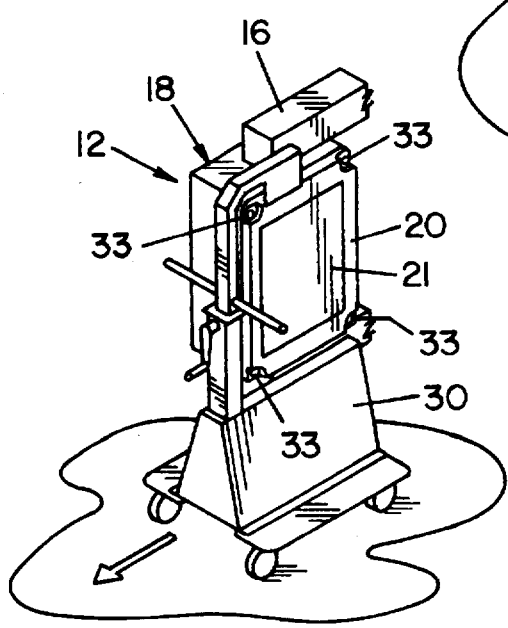
FIG. 3C is a perspective view similar to FIGS. 3A and 3B showing the cart transferring the collimator to the gamma camera's detector head.

Referring now to FIGS. 3A, 3B, and 3C, there is shown an arrangement where a transfer cart 30 slides into a storage rack module 31 (only one module is illustrated) which contains any specific collimator 21. Transfer cart 30 slides over collimator frame 20, grasps collimator frame 20 and removes collimator frame 20 with its collimator 21 from storage rack module 31. As shown in FIG. 3B, transfer cart 30 is then moved into gamma camera 10 which has rotated its detector heads 12 into a vertical position. As shown in FIG. 3C, transfer cart 30 slides collimator frame 20 onto detector head 12 (whose collimator has been previously removed by transfer cart in the reverse process) and collimator frame 20 is secured to detector head 12 by several swing out, wing nut fasteners indicated generally at reference numeral 33. Insofar as the present invention is concerned, FIGS. 3A–3C simply demonstrate that the face of the gamma camera, be it a collimator or the filter of the present invention, is easily applied and removed from gamma camera 10 during normal operation. Reference can be had to SMV's U.S. Pat. No. 5,381,012 for a detailed explanation of the transfer system.

Figure 4:
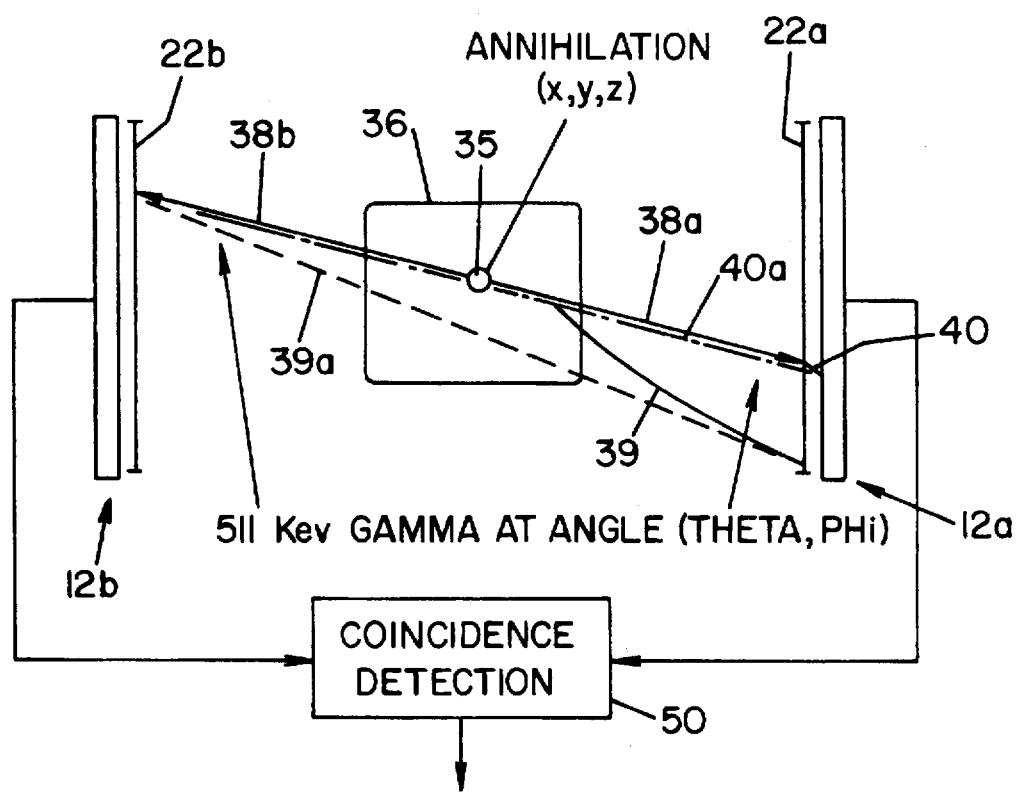
FIG. 4 is a schematic illustration of a positron annihilation event detected by the gamma camera.

Referring now to FIG. 4, there is schematically shown a positron annihilation event indicated by reference numeral 35 occurring within a body organ 36 of a patient. As is well known, positron annihilation 35 produces a pair of photons having photopeak energies of about 511 Kev traveling linearly opposite one another at the speed of light. Specifically, one photon traveling on path 38a will strike detector head 12a while its counterpart photon traveling on path 38b will strike the opposite detector head 12b. Generally, each detector head 12 will register a position where a photon impacted its surface and by correlating that incident position with the point where the opposing detector head was impacted by the other coincident pair photon, a line of response (LOR) passing through the positron annihilation event can be constructed. It is appreciated that the FDG will concentrate at certain portions of the body organ whereat a large number of positron annihilations will occur. By generating many LORs that portion of the body organ which is generating positrons from the FDG decay can be constructed by tomographic reconstruction techniques.

It is to be appreciated that in a PET scanner the line of response will be determined in a two-dimensional, x,y plane. In a gamma camera, the line of response has to be determined as a line in space, i.e., three-dimensional, x,y, z. It can be readily seen from FIG. 4 that many LORs, will escape through the free space between detector leads 12a, 12b. Thus, gamma camera 10 has a more complex problem in determining LORs than the conventional PET ring scanner (x,y,z vs x,y) with a sample of LORs that do not include all the LORs emanating from the patient.

It is known that many photons resulting from positron annihilations will experience Compton scattering. Compton scattering will principally occur either within body organ 36 of the patient or within scintillation crystal 22a. When a coincident pair photon is subjected to the Compton effect, its energy is attenuated and its line of flight changes. This is diagrammatically illustrated in FIG. 4 where the photon traveling on path 38a experiences Compton scattering within organ 36 and is deflected at a relatively high angel to travel somewhat nonlinearly on path 39. If the impact point of the Compton scattered photon on path 39 is used to generate a LOR as shown by dash-line 39a, an erroneous LOR will be generated. It is principally for this reason that many PET scanners will only operate to match coincident pair photons having spectral energies of about 511 Kev.

Compton scattering can also occur within scintillation crystal 22 and the path of a Compton scattered photon within scintillation crystal 22a is shown by reference numeral 40 in FIG. 4. The dot-dash LOR 40a resulting from a scintillation produced from a photon experiencing Compton scattering within scintillation crystal 22a is very close to the LOR produced by coincident pair photons which have not experienced any Compton scattering.

Figure 7:
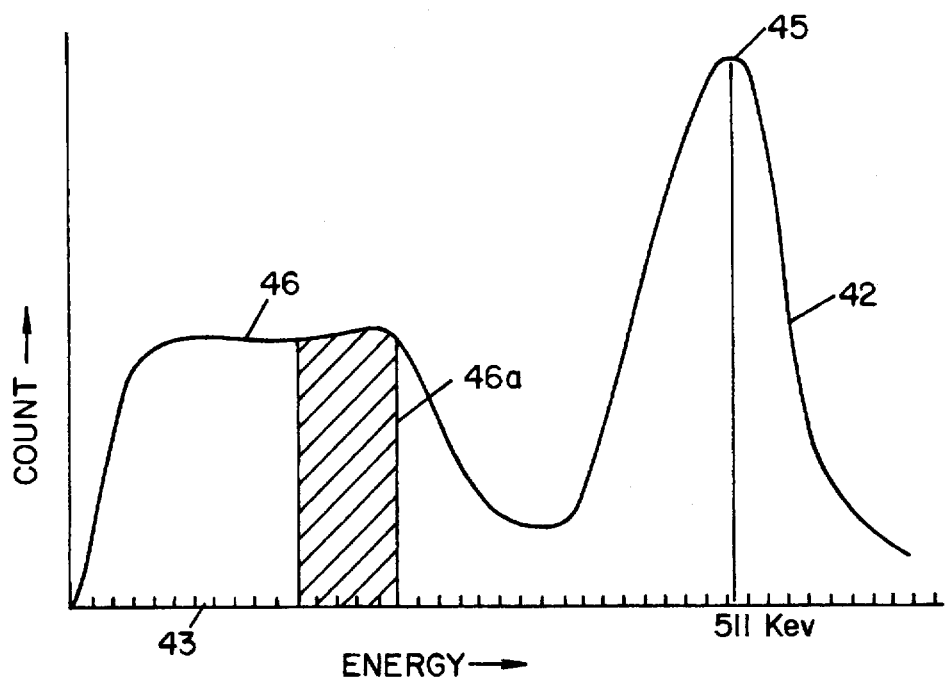
FIG. 7 is a graphical representation of a histogram derived from a multi-channel analyzer showing the counts recorded by a PMT.

It is of course known that when crystal 22 absorbs the energy of a photon, a scintillation is emitted from crystal 22 having an intensity correlated to the energy of the absorbed photon. When the photon experiences Compton scattering in the crystal and the Compton scattered photon is absorbed by the crystal, a scintillation will be produced having an intensity correlated to the attenuation Compton scattered photon. This is illustrated by the histogram graph 42 shown in FIG. 7. Histogram 42 is developed in a conventional way from a multi-channel analyzer having a number of channels 43 set at various scintillation photopeak energy ranges and the photopeak energy of each scintillation recorded by any PMT is recorded as a count in its appropriate energy range channel. Histogram 42 is what results when any given PMT is flooded with a source of positron producing energy. This known histogram 42 is characterized by a sharp peak 45 occurring at the photopeak energy of about 511 Kev which corresponds to the energy of a photon resulting from a positron annihilation and a flat peak portion 46, a portion of which 46a can be attributed to Compton scattering of a positron pair of photons. Of course, when detector 12 is flooded with the uniform source of positron producing radiation, the entire flat peak 46 can be attributed to Compton scattering. In practice, peak 46 represents stray radiation, Compton scattered radiation produced outside crystal 22 and Compton scattered radiation produced within crystal 22. If the counts or some part of the counts occurring in flat peak 46 can be attributed to Compton scattered radiation resulting within crystal 22, then the counts attributed to Compton scattering as well as those counts of high peak portion 45 can be used to establish LORs. The sample size of annihilation events recorded by gamma camera 10 can be significantly increased. In practice, good resolution images of a gamma camera performing a PET study can only be had if Compton scattered scintillations occurring within crystal 22 can be counted and matched with 511 Kev photopeak photon scintillations occurring in high peak portion 45 of histogram 42. This forms one of the underpinnings of the present invention. In this connection, it must also be noted that the inventors have not been able to discern any PSD technique which would permit differentiation or analysis of the scintillation stored in flat peak portion 46 which would distinguish photons undergoing Compton scattering outside the scintillation crystal from those which have undergone Compton scattering occurring within the scintillation crystal.

Generally speaking, scintillation crystals are selected by considering, among other factors, the density of the crystal and the thickness of the crystal. For any crystal of any given density which is subjected to a stream of radiation of a given energy, some percentage of the energy will pass through the crystal without absorption and some percentage of the radiation will be absorbed at various depths of the crystal. For example, if the crystal is ⅜" thick, the sodium iodide crystal might absorb 50% of technetium rays by the time the rays have traveled a distance within the crystal of ³⁄₁₆" and perhaps allow only 10% of the radiation to pass through the crystal. As the energy of the radiation increases, the distance from the face of the crystal at which any given percentage of the radiation is absorbed increases. If the crystal thickness is increased to cover higher energy radiation (assuming that the crystal thickness is increased so that only 10% of the higher energy radiation passes through the crystal without being absorbed by the crystal), then the point at which absorption occurs for the lower energy rays is shifted away from light tubes 23 resulting in loss of resolution. On the other hand, if the material for the crystal is changed from sodium iodide, then the intensity of the scintillation for a lower energy ray falls outside the preferred band width response or range of the PMT. This is exactly the problem which occurs when a gamma camera has to be operated to detect the lower energy radiation resulting in a SPECT study as well as the higher 511 Kev radiation in a PET study. PET scanners do not have the problem and typically use bismuth germinate (BgO) crystals which produce scintillations having intensities at the higher radiation energies well within the preferred response band range of the PMT while maintaining minimum crystal depth. Because gamma camera 10 of the invention has to operate for SPECT studies, the crystal composition or density has to be maintained at the level of the thallium doped sodium iodide crystal and in the preferred embodiment, the depth of the crystal is only slightly increased, i.e., about ⅛". As discussed, this increase will result in more 511 Kev scintillation counts than if the crystal's thickness was not increased at all. The NaI crystal thus absorbs a much higher portion of the attenuated radiation and significantly increases the count rate of the camera even without considering the Compton scattering of the attenuated radiation in the crystal. This forms another underpinning of the invention.

Thus, the filter plate of the invention permits the use of a NaI crystal in PET studies without experiencing any significant decrease in the ability of the crystal to absorb and produce scintillations for the 511 Kev photons while the crystal can still operate effectively for SPECT studies.

Referring still to FIG. 4, when and as each detector head 12a, 12b senses a photon scintillation, that signal is sent to a coincidence detection circuit 50 which is conventional and is used in many PET scanners. Coincidence detection circuit 50 determines whether any given signal from a detector from one detector head occurs within a very short time window of a signal from the other detector head and if so, matches or pairs those two signals. Since the detector head established the position where those signals originated and the coincidence detection circuit 50 matches two signals into a coincidence pair, a line of response is established and number of the line of responses are accumulated and processed to produce a tomographic image.

Figure 5:
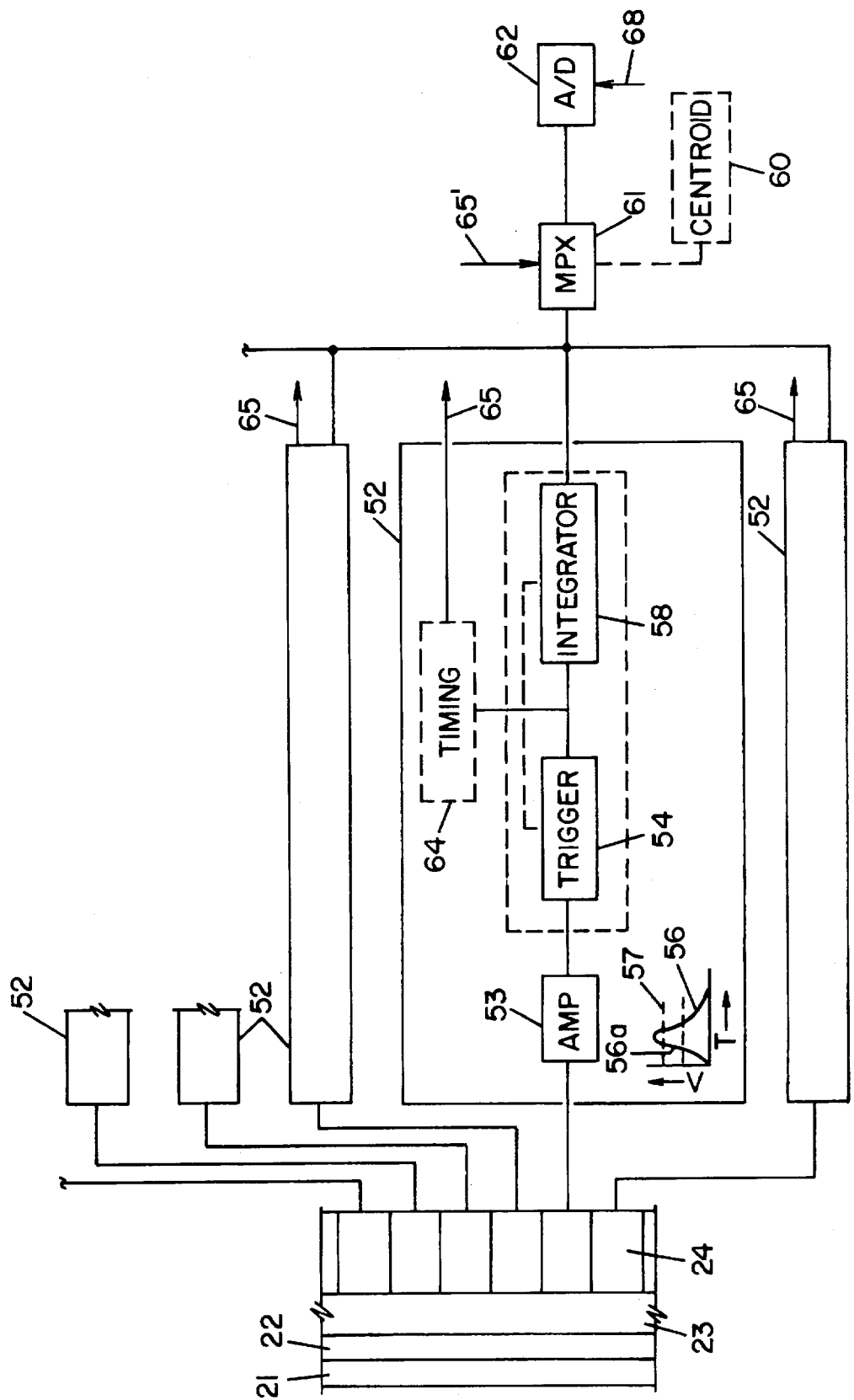
FIG. 5 is a schematic illustration of a portion of the signal processing components used in a gamma camera employing the invention.

FIG. 5 is a general schematic showing in somewhat more detail how gamma camera 10 is modified to develop the timing signals inputted to the coincidence detection circuit 50. Each PMT 24 has a triggering circuit 52. Each pulse signal is amplified at amplifier 53 which signal is then sent to a conventional triggering circuit 54. Triggering circuit 54 can best be explained by reference to photopeak curve 56 which is the shape of the electrical pulse generated by the PMT in response to a scintillation. While triggering circuit 54 can take several different forms, in the preferred embodiment, the initial rise 56a of photopeak curve 56 is checked through a dv/dt circuit to make sure there is a fast enough change, i.e., a steep rise, at the leading edge of the pulse to indicate a scintillation event. Then, a software set triggering voltage level 57 is required to be exceeded by the voltage of the pulse. Triggering voltage level 57 is typically set at a slightly higher level for a PET study than that which it would be set at for an SPECT study. More specifically, triggering voltage level 57 would be set at a value sufficient to record the energy levels of scintillations produced from positron annihilation photons which have undergone filter attenuation and then further attenuation attributed to Compton scattering. When a PMT pulse signal triggers triggering circuit 52, it then becomes the triggering pulse signal which is sent to an integrator 58 which integrates the signal to arrive at an analog signal indicative of the intensity of the scintillation. Triggering circuit 52 also advises a centroid calculator 60 of the fact that it has become a triggering pulse signal and centroid calculator 60 instantaneously actuates the integrator 58 for a preset plurality of adjacent PMT pulse signals. The triggering pulse signal along with the adjacent PMT pulse signals are grouped or bundled together at a multiplexor 61 and then sent as a bundled string of analog signals to analog to digital converter 62 whereat the signals are digitized into a bundle of digitized data signals which are then further refined by weighting and corrected by calibration look up tables to produce position and intensity signals. When the camera is operated in its SPECT mode, the signals form pixels for scintigrams. When the gamma camera is operated in its PET mode, the position on the detector head for the LOR is established.

The conventional gamma camera triggering circuit 52 as thus described is modified for PET studies by the inclusion of a triggering timing circuit 64. When triggering circuit 54 generates a triggering pulse signal as discussed above, that triggering pulse signal activates triggering timing circuit 64 to generate a timing signal 65. Timing circuit 64 can take any number of forms. In the preferred embodiment timing circuit 64 is simply a constant fraction discriminator in combination with a zero crossover detector. Other arrangements will suggest themselves to those skilled in the art.

Figure 6:
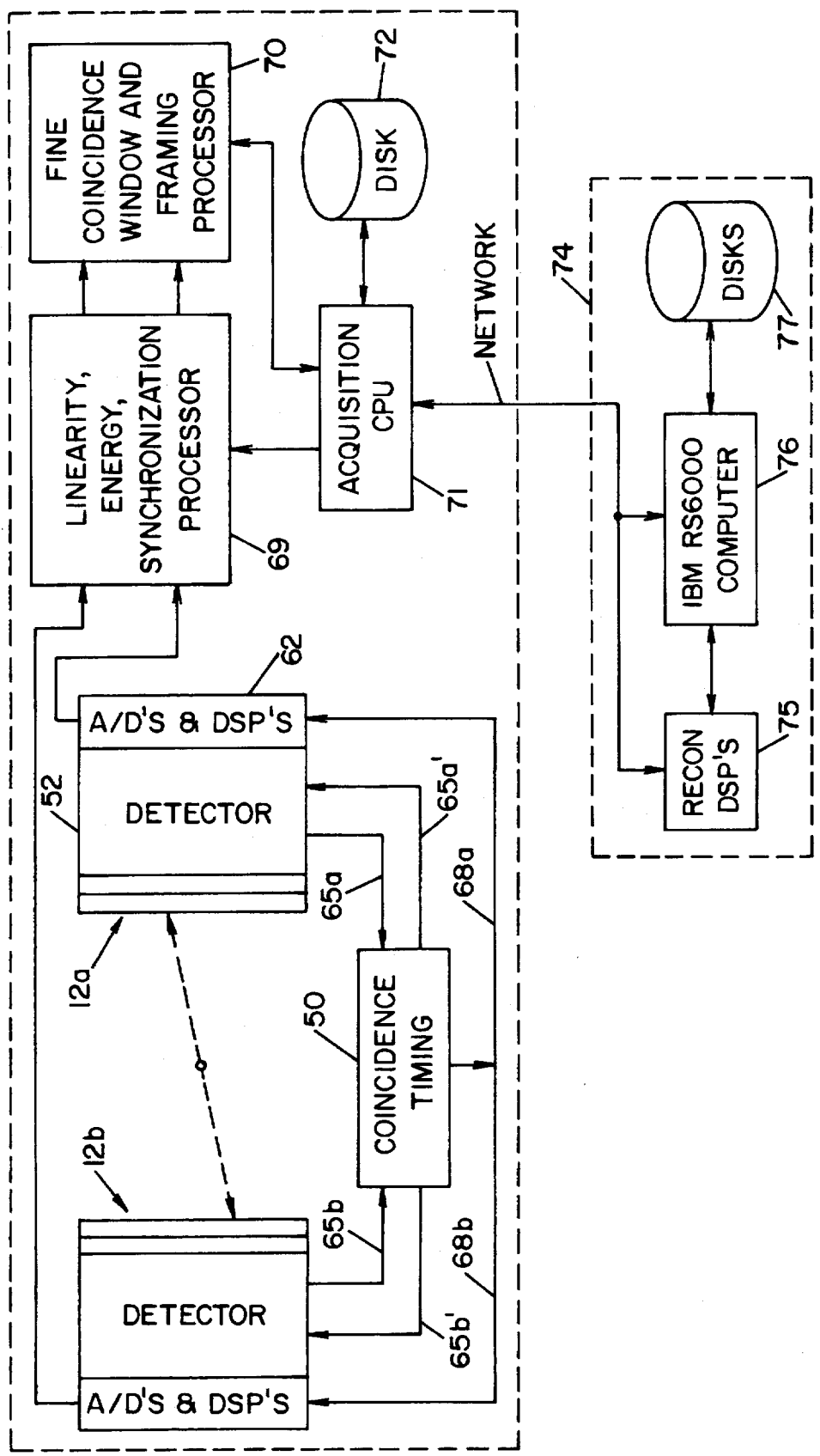
FIG. 6 is a schematic illustration in greater detail than that shown in FIG. 4 of the signal processing components used in the camera to perform a PET study.

Referring now to FIG. 6, the overall processing arrangement is shown in greater detail. Triggering signal 65a for detector head 12a and triggering signal 65b originating from detector head 12b are sent to coincident detector circuit 50 for detection as described above. When a coincident photon pair is detected and matched, the matched triggering signals now 65a', 65b' are returned to multiplexor 61 for gating or releasing bundled string of integrated analog signals corresponding to the triggering pulse signal to analog to digital converter 62. If any triggering signal either 65a or 65b is not matched, coincidence timing circuit 50 instructs centroid 60 of this fact and the bundled signals correlated to that triggering pulse signal is discarded. Coincidence timing circuit 50, in addition to gating the bundled analog pulse signals, also develops a digitized time stamp signal 68a, 68b which is sent to each detector heads analog to digital converter 62 and is processed along with the bundled pulse signals.

FIG. 6 also illustrates the general processing approach. Each bundled signal is corrected and refined through a series of refinement digital signal processors 69 and then through a series of timing digital signal processors 70, both digital signal processors 69, 70 under the control of an acquisition CPU 71. Refinement digital signal processors 69 correct the linearity and energy through a series of weighting calculations with corrections done through look up tables generated during calibration. Essentially, refinement digital signal processors 69 produce a weighted and corrected x,y position on detector head 12 where the scintillation event occurred and a corrected photopeak voltage for each scintillation. Timing digital signal processors 70 correct the time stamp signals and verify that at the corrected positions, a scintillation event occurred within the given time window (shorter than that established by coincidence timing circuit 50). Importantly, the corrected energy levels of each coincident pair is checked to make sure that a 511 Kev scintillation event matches another 511 Kev scintillation event or a Compton scattered event. If the energy in fine coincidence window requirements are met, acquisition CPU 71 stores the LOR data onto disk 72 or, alternatively, the information can simply be passed through to a tomographic reconstruction station 74 which uses reconstruction digital signal processors 75 under the control of a computer 76 which builds tomographic reconstruction images stored onto disk 77. For SPECT imaging, digital signal processor 69 essentially produce the pixel data used to construct the scintigrams.

As thus described, gamma camera 10 can be set to trigger and collect data for SPECT studies as well as PET studies. Further, for PET studies, valid positron annihilation events are counted if a photon produced scintillation having unfiltered photopeak energy of approximately 511 Kev is matched with a scintillation event occurring at the other detector head having unfiltered photopeak energy of 511 Kev or a lesser photopeak energy attributed to the Compton effect. From the preceding discussion with reference to FIG. 4, it is clear that if a gamma camera was operated in this manner, and without more, photons undergoing Compton scattering within body organ 36 would result in totally unreliable data and gamma camera 10 would be inoperable for a PET study.

Figure 9:
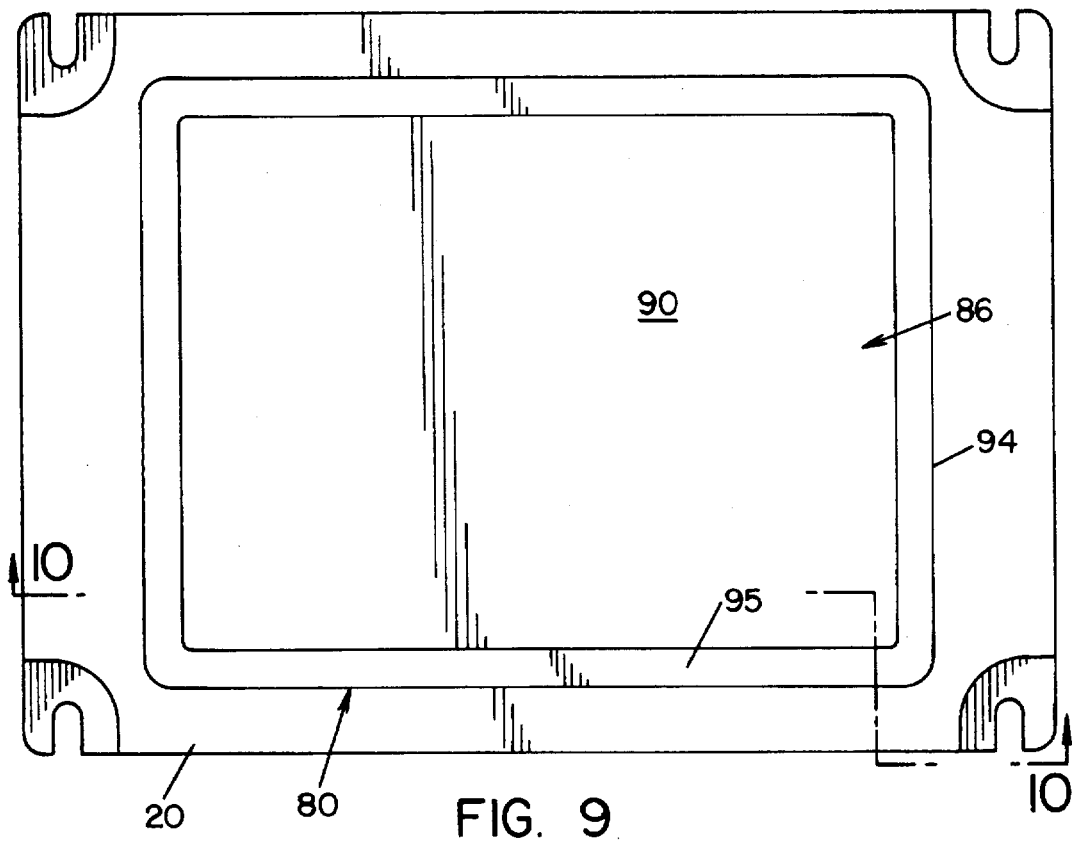
FIG. 9 is a plan view of the filter of the invention.
Figure 10:
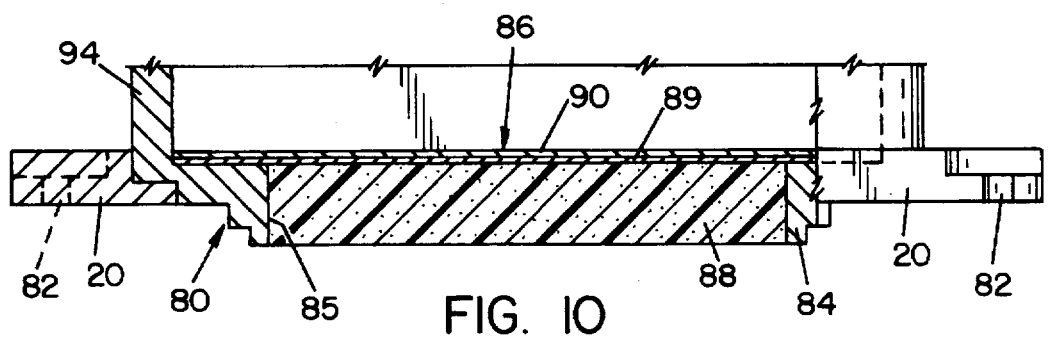
FIG. 10 is a cross sectioned view of the filter of FIG. 9 taken along lines 10—10 thereof.

Gamma camera 10 of the present invention overcomes this problem by means of a prefilter 80. As best shown in FIGS. 9 and 10, the conventional aluminum collimator frame 20 (with slots 82 for receiving wing nut fasteners 33 as discussed above) is fitted with a lead/5% antimony cast shield 84. Cast lead shield 84 has a rectangular opening 85 coincident with that of detector housing 18 and a depth equal to the minimum depth of the thinnest collimator 21. Spanning rectilinear opening 85 is a thin filter plate 86 secured to a recess formed at the front of cast lead shield 84. A closed cell polyethylene foam 88 extending the depth of cast lead shield 84 and spanning opening 85 is provided to support filter plate 86.

In the preferred embodiment filter plate 86 comprises a bottom lead sheet 89 approximately 0.02" thick glued to a half hard copper sheet 90 approximately 0.08" thick. Filter plate 86 is designed to filter out radiation having spectral energies equal to that of positron annihilation photons which have undergone Compton scattering. In the preferred embodiment, filter plate 86, which is a graded plate composed of at least two layers will essentially absorb radiation having spectral energies producing photopeak pulses of about 250 Kev or less. Those skilled in the art understand that absorption of radiation by filter plate 86 is a function of the atomic number Z (effective atomic number when graded plates are used) and the edge thickness of the layers of filter plate 86. (For example, see half value layers for various materials such as that set forth in an April, 1968 publication of the U.S. Department of Health, Education and Welfare, entitled "*Half Value Layers at Photon Energies from 10 Kev to 10 Mev*", by Gerald L. Rhinehard and Norman F. Modine.) It is only necessary for filter plate 86 to reduce the spectral energy of the radiation impacting scintillation crystal 22 to a photopeak voltage less than triggering voltage level 57 set at triggering circuit 54. Other filtering arrangements will suggest themselves to those skilled in the art.

Figure 8:
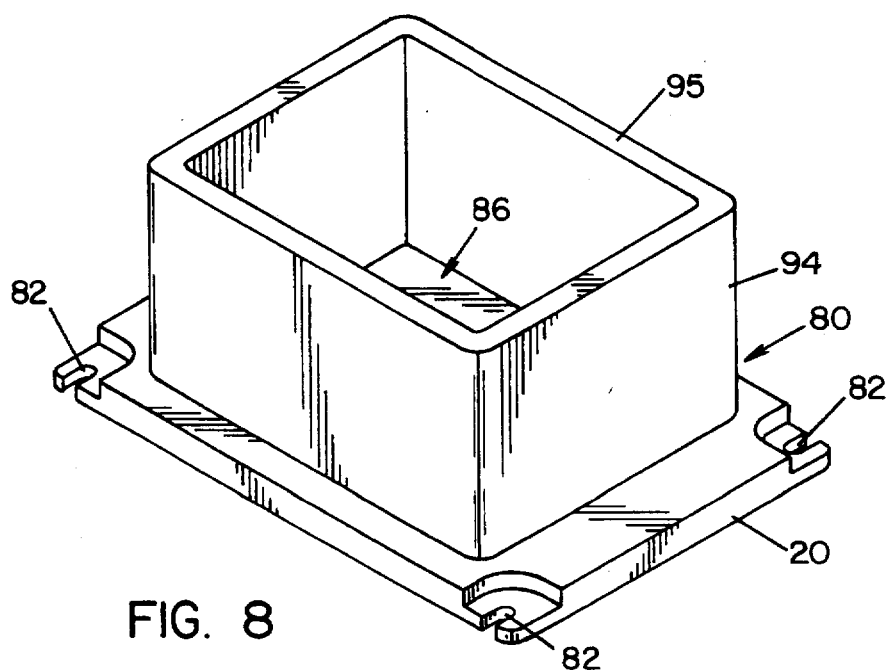
FIG. 8 is a perspective view of the filter of the present invention.

Referring now to FIG. 8, cast lead shield 84 is molded with an integral baffle 94 circumscribing filter plate 86 and protruding forward from the front of collimator frame 20. When conducting a PET study, the forward edge 95 of baffle 94 will be moved as close as possible to the patient's body organ 36. In theory, the invention can and should work without baffle 94. In practice, a significant amount of stray radiation of 511 Kev has been experienced in operation of gamma camera 10. This is believed attributed to the presence of PET scanners in other rooms adjacent to that housing the gamma camera which radiation passes through walls, etc., and surprisingly finds its way to the gamma camera. (Stray radiation at 511 Kev does not adversely affect gamma camera 10 during SPECT studies because of the high energy levels which can be disseminated and discarded in trigger circuit 52). When detector heads 12 were shielded by baffle 94, a marked increase in camera resolution, was noted. A lead/antimony baffle 94 is a convenient way to shield detector heads 12 from stray 511 Kev radiation. Other shielding/shroud arrangements will suggest themselves to those skilled in the art.

The invention has been described with reference to a preferred embodiment. Obviously, modifications and alterations will suggest themselves to one skilled in the art upon reading and understanding the Detailed Description of the Invention. It is intended to include all such modifications and alterations insofar as they come within the scope of the present invention.

Having thus defined the invention, it is claimed:

1. A gamma camera for performing PET studies in which a patient has ingested or been injected with a radiopharmaceutical emits positrons, each positron undergoing an annihilation which produces a pair of photons, each photon traveling in a linear opposite direction to the other and each having a photopeak energy of about 511 Kev, some photon pairs having a photon striking a first detector head of said camera while the opposite traveling photon strikes a second detector head of said camera, said patient positioned between said first and second detector heads, said camera comprising:

a) each detector head having a scintillation crystal and a plurality of photomultipliers adjacent one another on one side of said crystal producing pulse signals indicative of the intensity of scintillations produced by said crystal when struck by said photons;

b) signal triggering means for determining when said pulse signal of any given photomultiplier becomes a triggering signal having at least a set photopeak energy;

c) coincidence detecting means for determining when any given triggering signal from one detector head occurs within a preset time of any given triggering signal from the other detector head to establish a matched pair of triggering signals indicative of a positron annihilation event;

d) processing means for correcting and refining each matched pair of triggering signals so that tomographic images can be produced therefrom; and e) each crystal having on its side opposite that adjacent said photomultipliers, a filter extending over the area of said crystal, said filter having an atomic number Z and thickness sufficient to reduce the photopeak energy of photons resulting from positron annihilations which have experienced attenuation attributed to Compton scattering to a value not detected by said signal triggering means whereby photons having photopeak energies of about 511 Kev which experience attenuation attributed to the Compton effect within said crystal actuate said signal triggering means to increase the count of the positron annihilation events.

2. The camera of claim 1 wherein said filter substantially absorbs gamma radiation attributed to positron annihilation which has experienced attenuation attributed to the Compton effect.

3. The camera of claim 1 wherein said filter substantially absorbs about 250 Kev of photopeak energy of gamma radiation striking said filter.

4. The camera of claim 1 wherein said signal triggering means is set to detect pulse signals having photopeak energies in excess of about 250 Kev.

5. The camera of claim 1 wherein said crystal is NaI.

6. The camera of claim 1 wherein each detector head includes a body housing containing said crystal and said photomultipliers and a frame removably secured to said body housing, said frame containing said filter and having a continuous, shielding baffle circumscribing said filter adjacent the peripheral edge of said filter and protruding away from said body housing whereby said baffle is adapted to be positioned in close proximity to the imaged patient's body organ for shielding said detector head from stray radiation.

7. The camera of claim 6 wherein said baffle is substantially lead.

8. The camera of claim 1 wherein each detector head includes a body housing containing said crystal and said photomultipliers and a frame removably secured to said body housing, said filter includes a thin copper sheet facing said crystal and a thin lead sheet glued to said copper sheet facing the patient, said copper sheet and said lead sheet anchored within a lead/antimony mounting, said mounting secured to said frame.

9. In a gamma camera having first and second detector heads between which a patient is placed, each detector head having a scintillation crystal and a plurality of photomultiplier tubes adjacent the crystal side away from said patient; triggering means for sensing and determining which photopeak pulse signals generated by each photomultiplier are to be processed as triggering signals; coincident detecting means for sensing when photons produced by a positron annihilation event simultaneously strike each detector head and matching their respective triggering signals into matched pairs and signal processing means for forming tomographic images from a plurality of matched triggering signals when detected by said coincident means, the improvement comprising:

each crystal having on its side facing said patient a filter adjacent thereto and extending over the area of said crystal, said filter having an effective atomic number Z and a thickness sufficient to reduce the photopeak energy of photons resulting from positron annihilations which have experienced attenuation attributed to the Compton effect to a photopeak energy not sensed by said triggering means whereby photons resulting from positron annihilation events which experience attenuation attributed to the Compton effect within the crystal are detected as positron annihilation events by said triggering signal means.

10. The improvement of claim 9 wherein said filter substantially absorbs about 250 Kev of photopeak energy of gamma radiation striking said filter.

11. The improvement of claim 9 wherein each detector head includes a body housing containing said crystal and said photomultipliers and a frame removably secured to said body housing, said frame containing said filter and having a continuous, shielding baffle circumscribing said filter adjacent the peripheral edge of said filter and protruding away from said body housing whereby said baffle is adapted to be positioned in close proximity to the imaged patient's body organ shielding said detector head from stray radiation.

12. The improvement of claim 11 wherein said baffle is lead.

13. The improvement of claim 9 wherein each detector head includes a body housing containing said crystal and said photomultipliers and a frame removably secured to said body housing, said filter includes a thin copper sheet facing said crystal and a thin lead sheet glued to said copper sheet facing the patient, said copper sheet and said lead sheet anchored within a lead/antimony mounting, said mounting secured to said frame.

14. The improvement of claim 9 wherein said crystal is a thallium doped sodium iodide crystal about ½" thick.

* * * * *